United States Patent [19]

Van Riper et al.

[11] 4,337,377
[45] Jun. 29, 1982

[54] BIOLOGIC APPARATUS

[76] Inventors: Wilbur E. Van Riper, 2902 Fernwood Dr., Santa Ana, Calif. 92706; Virgil R. Laul, 709 S. Parton St., Santa Ana, Calif. 92701

[21] Appl. No.: 110,981

[22] Filed: Jan. 10, 1980

[51] Int. Cl.³ .......................................... H04M 11/06
[52] U.S. Cl. .................................. 179/2 R; 128/904; 179/2 DP
[58] Field of Search ................... 179/2 R, 2 A, 2 DP; 128/419 PT, 697, 706, 901, 903, 904

[56] References Cited

U.S. PATENT DOCUMENTS

| | | | |
|---|---|---|---|
| 3,426,150 | 2/1969 | Tygart | 128/904 X |
| 3,742,938 | 7/1973 | Stern | 128/904 X |
| 3,870,035 | 3/1975 | Sarnoff | 128/904 X |
| 3,872,252 | 3/1975 | Malchman et al. | 179/2 A |
| 3,882,277 | 5/1975 | DePedro et al. | 128/904 X |
| 3,910,260 | 10/1975 | Sarnoff et al. | 128/904 X |
| 4,121,573 | 10/1978 | Crovella et al. | 128/903 X |
| 4,141,351 | 2/1979 | James et al. | 128/904 X |

OTHER PUBLICATIONS

Electrocardiograms by Telephone—Crouch et al.—Bell Laboratories Record, Feb. 1966, pp. 43–47.
Translephonoe observation of implanted cardiac pacemakers—Furman—Medical Instrumentation, vol. 7, No. 3, May–Aug., 1973, pp. 196–202.
Webster's Third New International Dictionary—G. & C. Merriam Co., copyright 1961—p. 480.
Radio Shack® Dictionary of Electronics—second printing, 1974, p. 184.

*Primary Examiner*—Stuart N. Hecker
*Attorney, Agent, or Firm*—Francis X. LoJacono

[57] ABSTRACT

The present invention relates to a biologic apparatus that permits easy and quick telephonic transmission of biologic signals—such as an electrocardiogram, blood pressure, cranial waveforms, and the like—from any location having a telephone handset. The disclosed apparatus is so simple to use that, if necessary, an inexperienced person can perform the entire procedure.

The disclosed apparatus comprises a single, small, lightweight unit that may be carried unobtrusively in a purse, a handbag, a brief case, an attache case, or the like; and may be put into use at any location having a telephone handset.

It does not require cardiac-gel, and may therefore be used as often as necessary without causing skin problems. Furthermore, it obviates "hard-wiring" between the patient and the apparatus; so that there is no danger of pulling off electrodes.

12 Claims, 5 Drawing Figures

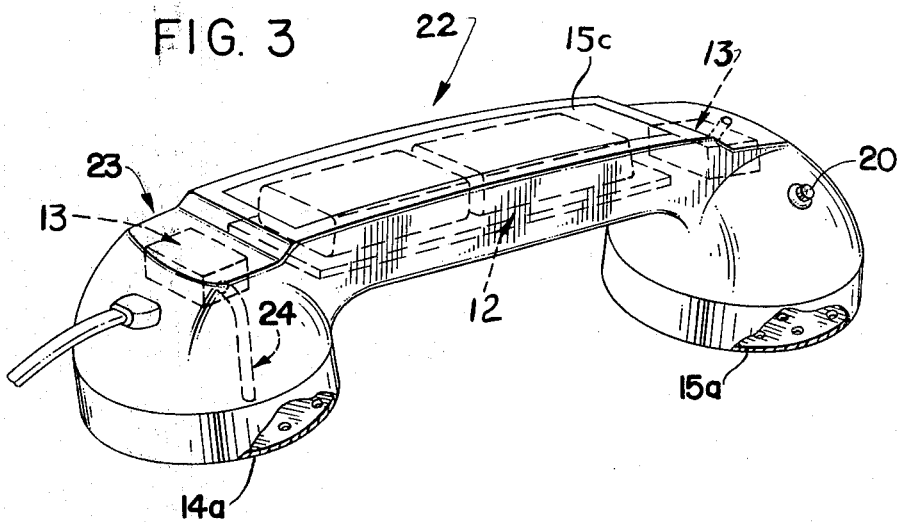
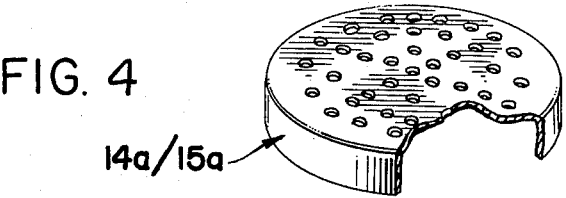
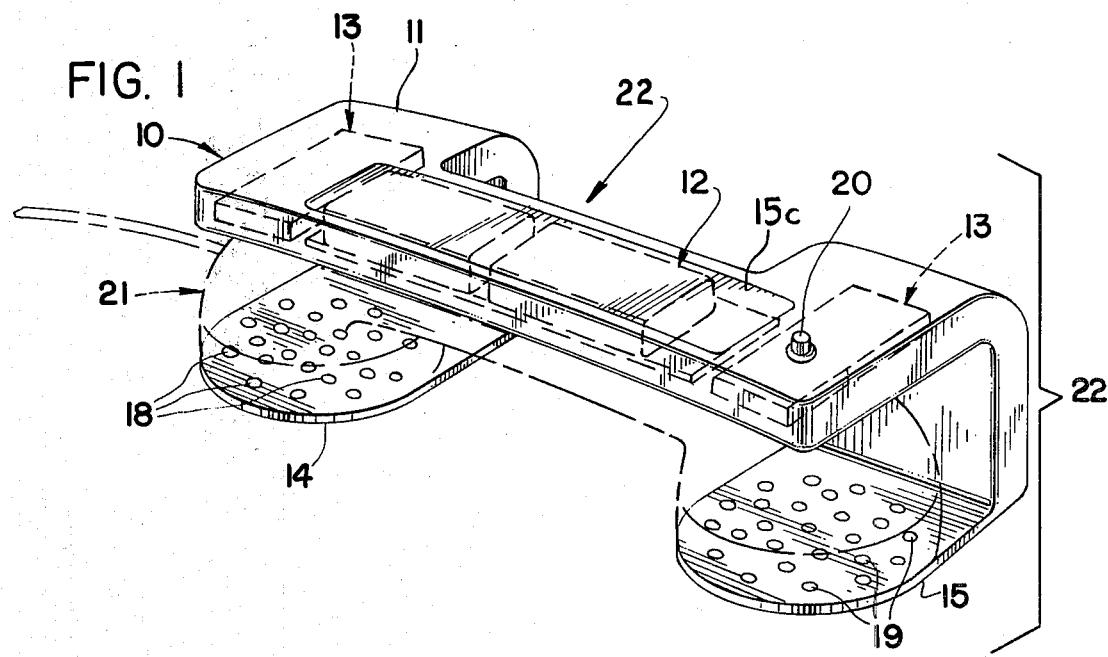

BIOLOGIC APPARATUS

BACKGROUND OF THE INVENTION

For ease of comprehension, the subject invention will be disclosed in terms of a cardiac-signal apparatus; but this is not to be construed as a limitation, as other uses will be discussed during the disclosure.

It is well known that near miracles are being performed in the treatment of heart difficulties; but it is not as well known that many serious cardiac distresses are encountered in post-treatment situations. These cardiac distresses may range from actual cardiac seizures, through relatively unimportant cardiac misfunctions, to groundless fears brought on by other unrelated conditions.

Such cardiac distresses may arise at any time or place—at home, while walking, while boating, in restaurants, at meetings, etc. Of course, a doctor should be contacted immediately; but, too often, the patient tends to wait out the cardiac distress. Some of the reasons for the waiting-out period are the desire not to bother the doctor, the possible embarrassment of reporting false symptoms, the fear of facing the actual cardiac review, etc. However, when a patient does contact the doctor, there is generally a need for a cardiac waveform—known as an EKG or an ECG; and this requires a rush trip to a hospital, medical office, or the like. Thus, a patient's fear of a cardiac-distress situation is worsened by an incipient panic situation and its attendant expense.

There are approximately 500,000 coronary deaths each year in the United States; and fifty to seventy percent of these are classed as "sudden" deaths. "Sudden death" is defined as death occurring within twenty-four hours of the onset of acute symptoms which begin outside of a hospital.

The cause of death in most of cases is due to ventricular arrythmia, which if detected earlier might have been avoided.

One of the basic instruments used by a doctor in the identification and treatment of heart disease is the electrocardiograph (EKG).

The EKG detects the electrical potentials generated by the action of the heart muscle. The permanent record of them is called an electrocardiogram.

Cardiographic analysis of a person with heart disease is frequently made at all stages of the disease.

When a patient is convalescing from one or a series of heart attacks or past heart surgery, the doctor may wish to obtain a daily or weekly electrocardiogram in order to check on his progress.

This usually requires that the patient go to the doctor's office or to a hospital for tests. This may be difficult, as well as expensive for a patient, particularly if he is in a physically and emotionally weakened condition.

It frequently happens that a person is stricken by a heart attack at work, at home, at a restaurant, on a boat, in an airplane or other inconvenient location. In most of these cases, an electrocardiogram could not be readily made.

Most people, even those with a history of heart disease, hesitate to call their phyician at the onset of symptoms. The reasons for this are many and varied. Sometimes, they do not want to bother him, particularly if it is late at night, or on a weekend—and think it is probably nothing anyway. Many, particularly elderly patients, do not call the hospital or physician because it takes much effort to go to the doctor or to a hospital.

There are numerous prior-art apparatuses that attempt to solve the above problem by sending the patient's EKG over the telephone system. Invariably, the proposed solutions require chest electrodes that utilize a cardiac gel; they generally require "hard-wiring" between the electrodes and the apparatus; and they require a conversion apparatus that converts the cardiac signal (from the electrodes) to a cardiac sound. The conversion apparatus usually comprises a cradle for a telephone handset; and the proper cradling of the handset applies the cardiac sound to the handset mouthpiece for telephonic transmission. Attention is directed to U.S. Pat. Nos. 3,426,150; 3,769,956; 3,872,251 and 3,872,252.

While these prior-art apparatuses improve the patient's mobility, they require that he carry around numerous and relatively burdensome components.

Other proposed apparatuses suggest the use of a radio transmission—which requires even more complex apparatuses.

These apparatuses have a number of objectionable features. The first objectionable feature is that they require the use of a cardiac gel smeared onto the patient's chest where the electrodes are to be placed. Cardiac gels are used to reduce the "interface" electrical resistance between the patient's skin and the electrode proper, in order to encourage the flow of the minute electric current that forms the electric cardiac signal. Unfortunately, cardiac gels tend to be irritating to the skin; and a person who requires frequent applications of the cardiac gel soon develops a painful skin condition.

A second objectionable feature of the prior-art apparatuses is the use of electrodes that are intentionally small—so that they may pick up cardiac signals from precisely designated body areas—this often being desirable for precise diagnosis, because the EKG varies somewhat with the location of the electrodes. Thus, incorrect placement of the small electrodes used by the prior art apparatuses may produce an undesired EKG.

A third objectionable feature of the prior-art apparatuses is the presence of hard-wiring extending from the electrodes on the patient's chest to the conversion apparatus. Even though these wires are made as flexible as possible, they must be strong enough for repeated use. As a result, patient movement or lack of care by the attendant may pull off the small poorly-adhered electrodes.

Another objectionable feature of the prior-art apparatuses is that the patient has to carry several pieces of equipment plus electrodes and gel.

Still another objectionable feature is that the patient has to assemble the apparatus, plug in leads, put gel on leads, attach leads to the chest, set several controls on the equipment; and cradle the telephone on the equipment.

Still another objectionable feature is the need to set various switches and pushbuttons, etc.

Still another objectionable feature is the need for an experienced attendant, if the patient's condition is such that he cannot direct the activities.

A still other objectionable feature is that the patient must purchase a relatively expensive apparatus, and must carry this bulky apparatus with him wherever he goes.

Thus, despite numerous proposed prior-art apparatuses, there is still a need for an improved cardiac-signal apparatus.

OBJECTIVES OF THE INVENTION

It is the principal objective of the present invention to provide an improved biologic apparatus.

It is another objective of the present invention to provide an improved biologic apparatus that is truly portable.

It is still another objective of the present invention to provide an improved biologic apparatus that does not require any hard-wiring between patient and apparatus.

It is a further objective of the present invention to provide an improved biologic apparatus particularly adapted for cardiac signals.

It is a still further objective of the present invention to provide an improved biologic apparatus adapted for immediate use by an unskilled or debilitated person.

It is a still further objective of the present invention to provide an improved biologic apparatus adapted to be used at any location having a telephone handset.

The attainment of these objectives and others will be realized from the following detailed description, taken in conjunction with drawings, of which:

FIG. 1 shows the basic inventive concept;

FIG. 3 shows a composite biologic module comprising a telephone handset and a biologic unit;

FIG. 4 shows pickup electrodes adapted for use with the composite biologic module.

SYNOPSIS

Figure 2:
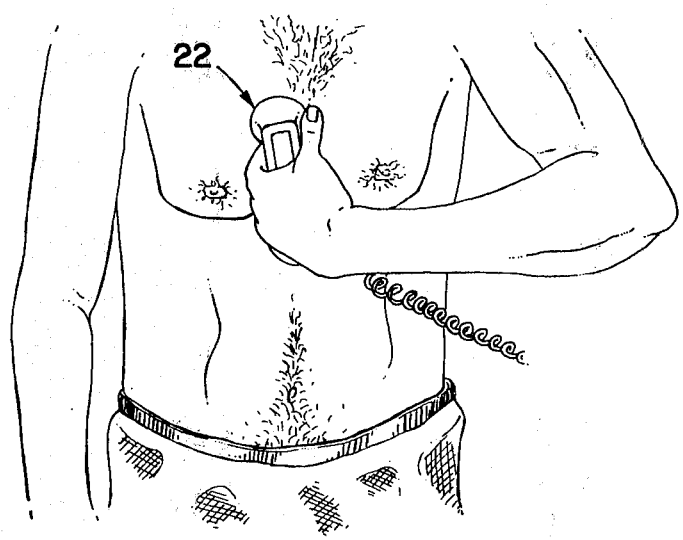
FIG. 2 shows how the invention is used.

Broadly speaking, the present invention discloses a truly portable biologic unit that is readily attached to a telephone handset, to form a hand-held biologic module. When the disclosed apparatus is to be used on a cardiac patient, the biologic module comprises a pair of integral, fixedly positioned, suitably spaced, pickup electrodes that are positioned to straddle the heart area. The disclosed apparatus inherently picks up an electric cardiac signal; converts it to a modulated cardiac sound; and transmits this over the telephone system to a receiver station.

When the resultant EKG has been analyzed, the operator at the receiver station actuates an "alert" tone at the biologic module, this tone alerting the patient to use the biologic module as a standard telephone handset to receive instructions.

INTRODUCTION

As indicated above, it is imperative for a cardiac patient to be able to transmit his EKG to a suitable receiver station; and this invention thus helps save the lives of people with heart trouble. Preferably, the transmitting apparatus should be so compact and lightweight that it may be carried at all times, and to any occasion that the patient chooses to attend.

Described is a portable, battery-operated biologic unit—comprising an electrocardiograph transmitter/receiver—that may be directly attached to the handpiece of a regular telephone. It is very easily operated at home or while traveling, and requires very little effort on the part of the patient. It clips directly onto the telephone handset, and requires no electrical leads of any kind connecting to the patient.

Heart-signal-pickup contacts are an integral part of the biologic unit; and, when the device is clipped in place, the heart signal electrodes fit over the telephone microphone and earpiece.

In order to send his EKG to his physician, hospital, or other suitable receiving center, all a patient has to do is to dial the appropriate telephone number, wait until the telephone is answered, identify himself, and indicate that he would like to send them his EKG.

The patient then would place the telephone handset directly on his bare chest or abdomen, and press a small pushbutton transmit switch on the biologic unit attached to the telephone. The EKG signal is picked up by the electrodes, is properly amplified, is filtered, and is converted to an audio tone (which is frequency modulated) and fed to a transducer. The transducer couples the signal into the microphone of the transmitting telephone handset. No hard-wiring is required between the phone and EKG.

When the receiving center begins to receive the transmitted EKG signal, the receiving telephone is attached to the EKG receiving device; and the EKG may be printed-out and/or displayed on an appropriate oscilloscope or other recording device. Upon receiving sufficient information from the patient, the receiver center operator sends an "alert"-tone signal back to the patient's telephone. This tone and/or a companion-light signals the patient that he is to remove the telephone EKG from his body, and to release the transmit-pushbutton switch.

Perforations in the electrodes permit normal use of the telephone while the EKG is attached to the telephone, but is not being used to transmit heart signals.

The patient then uses the telephone in a normal manner; and the receiving-station operator or physician could then tell him what action to take. The physician can tell whether or not the patient is in immediate danger. If the patient is indeed suffering from a heart attack, the physician can quickly dispatch an ambulance or paramedics to his aid, and instruct the patient or others close by as to what immediate action, if any, to take. If he is in no immediate danger, the physician may arrange for the patient to come to his office or to the hospital for a complete clinical EKG and examination.

One of the primary values of the invention, in addition to the obvious one of being a potential lifesaver, is that it will give the heart patient a much-needed sense of security and peace of mind. In having the new device readily available, he will know that his doctor and immediate help are only as far as the nearest telephone.

DISCLOSURE

The Biologic Unit

FIG. 1 shows a pictorial-and-phantom view of the biologic unit 10. Here, a suitable housing 11 encloses battery operated circuitry 12 comprising a sound producer 13 and other components which will be discussed later. The biologic unit 10 comprises a pair of cardiac-signal pickup electrodes 14 and 15 that are fixedly positioned and suitably spaced; and are an integral part of the biologic unit 10—no hard-wiring being used to connect them into the circuitry. As indicated, pickup electrodes 14 and 15 are perforated at 18 and 19.

A master/transmit switch 20 is positioned for convenient thumb actuation.

The pickup electrodes 14 and 15 are as large as convenient—typically ten to fifteen square inches, or the same area as the mouthpiece and the earpiece of a telephone handset.

The pickup electrodes 14 and 15 are preferably made of stainless steel, for a number of reasons. First of all, stainless steel retains its clean surface, so that it retains its low electrical resistance for interface contact with the skin. Secondly, stainless steel is not inimical to the skin; so that its use does not cause skin sores or abrasions. Thirdly, stainless steel is strong enough so that, once formed, it retains its configuration; and it does not bend or lose its configuration.

It so happens that the optimal electrode spacing for straddling the adult heart area is substantially the same as the mouthpiece/earpiece spacing of a telephone handset. Thus, the pickup electrodes 14 and 15 may be conveniently spaced so that they substantially coincide with the positions of these handset elements; and their size and shape may be substantially similar to these handset elements.

It should be noted, in passing, that the disclosed biologic unit may be used for children and for animals—in the latter case care must be taken to assure that the pickup electrodes are in actual contact with the skin.

As indicated in FIG. 1, the biologic unit 10 attaches to a telephone handset 21.

Here, suitable means—such as springs, the pickup electrodes themselves, resilient clasps or bands, Velcro, or the like—attach the biologic unit 10 to the handset 21.

It should be noted that the biologic unit 10 is dumbbell-shaped, and has a physical configuration that is similar and compatible to the physical configuration of the telephone handset 21; the physical configuration of unit 10 being defined by the oppositely disposed pickup electrodes 14 and 15 which are integrally interconnected by an intermediate portion of housing 11, the electrodes 14 and 15 being positioned adjacent the respective mouthpiece and earpiece of the telephone handset 21 and that, when they are attached, the biologic unit 10 and the handset 21 form a single compact biologic module 22 that is as easily hand held as a telephone handset by itself.

The sound producer 13 of the biologic unit 10 is preferably positioned in proximal relation to the mouthpiece of the telephone handset 21.

Use

It was pointed out above that the subject biologic unit was to be described in terms of a cardiac problem; but that it was also useful in other situations.

For this reason, the phrase "receiver station" will be used to designate any station that is adapted to receive and act upon the telephonically received biologic information.

FIG. 2 indicates how the disclosed biologic apparatus is used.

In use, the telephone is dialed to connect it with a receiver station; the reason for the call is stated—as by use of a code word; and the patient is identified. The patient is meanwhile baring his chest.

The telephone handset 21 and the biologic unit 10 are attached, as discussed above, to form the biologic module 22; and the biologic module 22 is positioned so that the pickup electrodes 14 and 15 straddle the heart area of the patient's chest, and pick up the electric cardiac signal.

When the master/transmit switch 20 is actuated, the circuitry 12 converts the electric cardiac signal from the pickup electrodes to a modulated cardiac sound at the sound producer 13, the modulated cardiac sound having audio characteristics that vary with corresponding characteristics of the EKG. The cardiac sound enters the mouthpiece of the telephone handset 21, and is transmitted over the telephone system to the receiver station. Here, the transmitted telephonic signal is transformed to a visual display and/or to a printout, and may be analyzed and/or computer-compared with previous data.

When the receiver station has completed its diagnosis, its operator transmits an "alerting tone" back to the patient's handset 21 that is still attached to the biologic unit 10; and this alerting tone alerts the patient that the receiver station desires to talk with him. The patient thereupon releases the master/transmit switch 20, and raises the entire biologic module 22—unit 10 and handset 21—to his ear and mouth. Because of the perforations in the pickup electrodes 14 and 15, the patient may now converse, without loss of time, with the personnel at the receiver station. The patient is now advised about the next procedure—be it a call to the doctor, administration of a predetermined medication, or a trip to a hospital.

In some cases—such as when a patient spends most of his time at a given location, or a location (i.e., a nursing home) where there are a number of patients—it may be desirable to leave the biologic unit 10 more or less permanently attached to the telephone handset 21

Alternatively, it may be desirable to incorporate the biologic unit into a modified telephone handset 23—as indicated in FIG. 3—that may be permanently connected to the telephone base, or may be plugable into a suitable telephone receptacle.

In a modified handset such as indicated at 23, it may be desirable to incorporate pickup electrodes 14a and 15a (FIG. 4) directly into the handset 23; and it may further be desirable to use a "sound tube" 24 to conduct sound from a differently positioned sound transducer to the mouthpiece portion of the handset.

Circuitry

Figure 5:
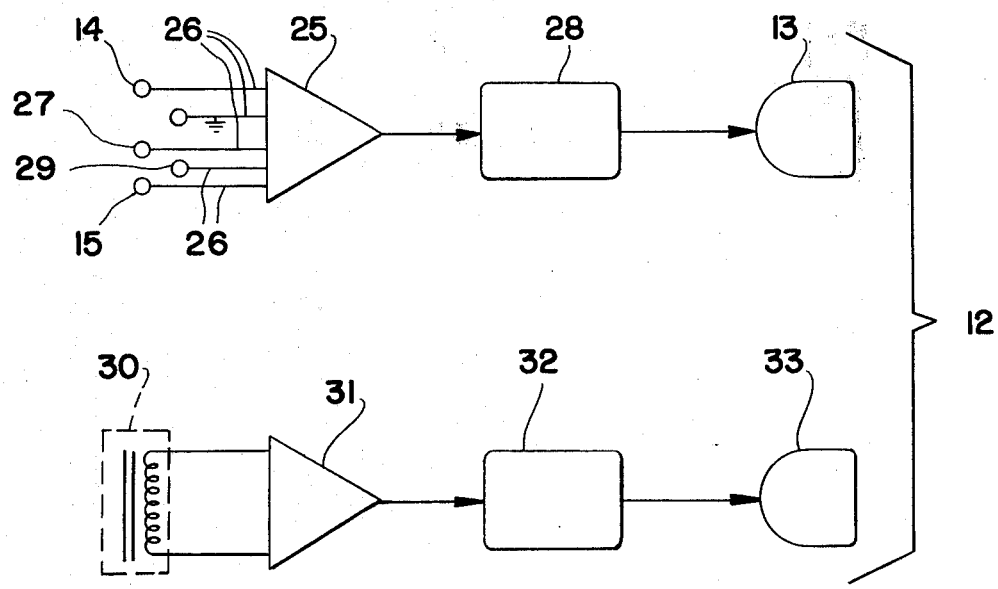
FIG. 5 shows pertinent circuitry.

FIG. 5 shows a partial block diagram of circuitry 12 for practicing the subject invention—although similar circuits (having their own particular advantages, disadvantages, and complexities) are shown in the prior art.

FIG. 5 indicates two pickup electrodes 14 and 15, the electric cardiac signal existing between them being applied to a differential amplifier 25 which is A.C. coupled to the electrodes in order to minimize the D.C. galvanic voltage developed as a result of the skin/electrode interface.

Attention is directed to the fact that the "connecting wires" 26 of FIG. 5 are only symbolic; the electrodes 14 and 15 are directly connected to the amplifier 25 without the use of exterior hard-wires.

If desired, a third or reference electrode may be incorporated into the biologic unit in order to improve the signal/noise ratio; the third electrode—if used—functions as a reference for the circuitry and for the patient.

The output of the differential amplifier 25 is applied to a voltage-to-frequency converter 28 that converts electric cardiac-signal variations (which comprise minute voltage fluctuations) to a frequency modulated electrical signal wherein the frequency fluctuations correspond to the voltage fluctuations of the original cardiac signal. The voltage-to-frequency converter 28 may comprise—for example—a two kilohertz oscillator whose two kilohertz signal is modulated by the fluctuating frequency of the cardiac signal. The unit 28 may further comprise bandpass limiters, amplitude limiters, and the like, in order to assure a frequency modulated signal that is readily handled by the telephone system.

The output of the voltage-to-frequency converter 28 is applied to sound transducer 13 that changes the frequency modulated electric signal to a varying-frequency two kilohertz FM signal that is acoustically coupled to the telephone-handset mouthpiece (not shown in FIG. 5).

Thus, the electric cardiac signal—as picked up by the electrodes 14 and 15—eventuates into a frequency modulated two-kilohertz cardiac signal that is well handled by the telephone system; and this telephonic signal is transmitted to the receiver station where it is recorded and/or analyzed, etc.

Alternatively, the cardiac signal may be transmitted over a radiotelephone, a citizens-band transmitter, or any other form of transmission equipment.

It was pointed out above that, while the present invention was to be presented in terms of a cardiac patient, the apparatus may be used for other purposes.

Alternatively, the input may come from another suitable sensor 29.

As indicated above, the receiver station produces an alert signal that is used to alert the patient that the EKG has been analyzed; and that the patient is to remove the biologic module from his chest, and to use the still-attached telephone handset for a normal telephonic conversation.

The receiver station may produce the alert signal by any of a number of circuits, such as a resonant or a frequency sensitive circuit that picks up a suitable signal—typically one kilohertz—from the many frequencies present at the receiver station handset. Alternatively, it may take the form of an independent oscillator. Other suitable circuits are known.

At this time the biologic module is being held against the chest area of the patient; and it is quite possible that the alert sound may be so muffled that the patient would not hear or recognize it. Therefore, the biologic unit comprises circuitry for detecting and amplifying the alert signal from the receiver station, and for producing a loud alert sound that cannot be missed. Such a circuit is indicated in FIG. 5, wherein a pickup device 30 picks up the alert signal from the receiver station; and applies this signal to amplifier 31, and—through a suitable filter 32—to an audio transducer 33 that produces a loud audible alert sound.

If desired, the alert sound may be replaced by, or accompanied by, a light that serves as an alert light.

SUMMARY

The use of the biologic apparatus is described in terms of cardiac problems; but the unit may also be used to transmit blood pressure, EMG, EEC, or other signals.

In use, the biologic unit is attached to a telephone handset so that the perforated pickup electrodes cover the ear and mouthpiece portions of the telephone handset. The patient "contacts" the reference electrode when he grasps the biologic module.

After the patient dials his physician or other facility equipped with an appropriate receiver, he identifies himself and indicates that he has some problem—such as chest pains, etc. The receiving center turns on their equipment, and tells the patient to send his EKG.

The patient does this by placing the biologic module directly on his bare chest or abdomen. He then depresses the single pushbutton switch which activates the transmitter and feedback receiver. If the patient has made proper contact with his body, his EKG signal is then being sent over the telephone system.

After the physicial and/or receiving-center personnel have recorded enough information, they send back an alert signal over the telephone line; this signal is picked up by the biologic module and causes it to emit an audible signal and/or a flashing light signal. This tells the patient to release the pushbutton switch; to remove the biologic module from his chest; and to use the phone in a normal manner to receive further instructions.

The patient does not have to remove the biologic unit from the telephone handset in order to use the phone normally because the pickup electrodes are perforated, and thus permit normal telephone use.

In some cases, such as when a patient is bedridden or spends most of his time at a given location, it may be desirable to have the biologic module permanently attached to the telephone.

In other permanent installations, such as inside a hospital or nursing home, the biologic unit is built right into the telephone handset or base of the telephone, thus forming a fixed installation.

ADVANTAGES

The disclosed biologic apparatus is very easy to use, and has minimal preparatory requirements.

A patient having the slightest distress symptoms can easily and quickly transmit his EKG or other biologic signals to a receiver station.

The disclosed apparatus is small—typically about eight inches long, two inches wide, and 1 inch high.

It is very lightweight—typically eleven ounces.

It may fit into a purse, a handbag, a briefcase, an attache case, or the like.

It is very unobstrusive, and may be carried anywhere. Its very presence reassures the patient.

It may be used anywhere where there is a telephone handset—in an airplane, in a boat, etc.; and this includes practically anywhere in the world.

Another important advantage is that an inexperienced person can use it successfully the very first time. A small label may provide the desired telephone number, and a picture of how it is attached and used.

As indicated above, the large stainless-steel pickup electrodes facilitate the use by an inexperienced person. For example, if this person should miss the optimal chest locations for the electrodes, the large-size electrode still provides a cardiac signal of useful amplitude and waveform. Moreover, if the inexperienced person should happen to reverse the locations of the two pickup electrodes, the only effect would be to transmit an inverted EKG; and the personnel at the receiver station would recognize this immediately.

The disclosed biologic unit is completely self-contained and does not need any external connections such as hard-wiring to the patient, or electrical wiring to a power socket. In the permanent integral embodiment, the unit may be powered by the telephone line. Moreover, the disclosed apparatus does not have any switches or pushbuttons that may be inadvertantly misset.

This invention is not intended to replace a regular clinical EKG as obtained by a physician. The main purpose of the device is to enable a patient to send a simple EKG to the hospital or physician for a quick analysis, and to do it very easily.

This invention will alleviate objections to prior-art devices, for patients can now send their EKGs to the hospital as easily as picking up their telephone. The unit may be taken by the patient on trips, in the automobile, on an airplane or anywhere else—because a doctor is as close as the nearest telephone.

The majority of cardiac arrhythmias occur either at work or at home. The new biologic apparatus is packaged into a portable form, which may be readily attached to a standard telephone handpiece, and may be carried by the patient wherever he goes.

It may, alternatively, be embodied as an integral part of a telephone or telephone-system handpiece. Or, it may be incorporated into almost any kind of radiotelephone, citizens-band transmitter or any other form of data-transmission equipment.

Another advantage of this invention is to simplify the transmission of biomedical signals (such as EKG signals) by untrained persons, even though they may be under undue stress and strain at the time of the transmission.

One of the principal advantages of the disclosed device is the elimination of the need for patient lead-wires of any kind.

For people undergoing a cardiac arrhythmia, it may be impossible to perform—particularly on very short notice while under the stress and strain of the attack. The present invention provides simplicity and ease-of-use under these conditions.

The extra large electrodes on this invention provide a very large skin-contact area, thus reducing the total skin resistance. This particular feature makes contact jelly for the electrodes unnecessary.

In use, the patient places the telephone handpiece, with the new device properly attached, against his chest and depresses the pushbutton switch on top of the unit. As long as the switch is held depressed—and the unit is held firmly on the chest or abdomen—an EKG signal will continue to be transmitted. It is not necessary that the biologic unit be removed from the telephone handset when it is not being used to transmit EKG signals.

The invention and its attendant advantages will be understood from the foregoing description; and it will be apparent that various changes may be made in the form, construction and arrangement of the parts of the invention without departing from the spirit and scope thereof or sacrificing its material advantages, the arrangement hereinbefore described being merely by way of example; and we do not wish to be restricted to the specific form shown, operating frequencies or uses mentioned, except as defined in the accompanying claims.

We claim:

1. A self-contained biologic unit having a physical configuration that is substantially similar to the physical configuration of a telephone handset;
    said composite biologic unit including converting means, comprising a sound transducer, for converting biologic signals to corresponding sound signals adapted to be transmitted over a telephone system; and
    sound-tube means for conducting sounds from said sound producer to the mouthpiece of said telephone handset.

2. A self-contained biologic unit having a physical configuration that is substantially similar to the physical configuration of a telephone handset;
    said composite biologic unit including converting means, comprising a sound transducer, for converting biologic signals to corresponding sound signals adapted to be transmitted over a telephone system;
    an earpiece and mouthpiece oppositely disposed to each other;
    a first pickup electrode fixedly and integrally attached within said biologic unit without hard-wiring interconnecting said pickup electrode and said converting means;
    a second pickup electrode fixedly and integrally attached within said biologic unit without hard-wiring interconnecting said second pickup electrode and said converting means, said first and second electrodes being adapted to pick up said biologic signals and transmit said signals to said converting means;
    said pickup electrodes being located in said earpiece and said mouthpiece portions respectively of said composite biologic unit.

3. The combination of claim 2, wherein said pickup electrodes are perforated.

4. The combination of claim 3, including means for causing said biologic unit to produce an alert tone, said alert tone producing means comprising pickup means for sensing an alert signal, amplifying means for amplifying said sensed alert signal, and sound-transducer means for transducing said amplified alert signal to a loud alert sound.

5. The combination of claim 2, including a third pickup electrode fixedly and integrally attached within said biologic unit to improve the signal/noise ratio to said converting means, without hard-wiring interconnecting said third pickup electrode and said converting means.

6. The combination of claim 2, wherein said pickup electrodes are provided with a substantially cup-shaped configuration.

7. The combination of claim 2, including means for causing said biologic unit to produce an alert tone when an alert signal is transmitted by a receiver station back to said unit.

8. A self-contained biologic unit having a handset formed substantially similar to the physical configuration of a telephone handset, said biologic unit comprising:
    a housing having an earpiece and a mouthpiece interconnected to an intermediate member;
    a sound transducer for converting biologic signals to corresponding sound signals adapted to be transmitted over a telephone system;
    a plurality of pickup electrodes attached in said housing and adapted to pick up said biologic signals and transmit said signals to said sound transducer, wherein said sound transducer is positioned proximal to at least one of said electrode pickups, without hard-wiring interconnecting said pickup electrodes and said sound transducer.

9. A self-contained biologic unit having a configuration adapted to receive a telephone handset therein, said biologic unit comprising:
    a housing having a substantially bell-shaped configuration;
    a first and second pickup electrode, each being adapted to pick up biologic signals and transmit said signals, said electrodes being formed on said housing and spaced from each other to substantially coincide with the respective position of the mouthpiece and earpiece of said telephone handset; said first and second pickup electrodes being integrally connected by an intermediate portion of said housing; and a sound transducer disposed in said housing for converting biologic signals received from said electrodes to corresponding sound signals adapted to be transmitted over a telephone system, without hard-wiring interconnecting said pickup electrodes.

10. A biologic unit as recited in claim 9, including a third electrode adapted to improve the signal/noise ratio to said sound transducer, said third electrode not hard-wired to said sound transducer.

11. A biologic unit as recited in claim 9, including battery-operated circuitry.

12. A biologic unit as recited in claim 9, including means for causing said biologic unit to produce an alert tone when an alert signal is transmitted by a receiver station back to said unit.

* * * * *